United States Patent [19]

Kieffer

[11] Patent Number: 4,582,949

[45] Date of Patent: Apr. 15, 1986

[54] PROCESS FOR THE PREPARATION OF AN AROMATIC HYDROCARBON MIXTURE

[75] Inventor: Eduard P. Kieffer, Amsterdam, Netherlands

[73] Assignee: Shell Oil Company, Houston, Tex.

[21] Appl. No.: 735,031

[22] Filed: May 17, 1985

[30] Foreign Application Priority Data

May 18, 1984 [NL] Netherlands .......................... 8401606

[51] Int. Cl.$^4$ ................................................ C07C 2/00
[52] U.S. Cl. ...................................... 585/312; 585/314; 585/322; 585/324; 585/415; 585/525; 585/533; 585/517
[58] Field of Search ............... 585/312, 322, 324, 329, 585/415, 525, 533, 517, 310

[56] References Cited

U.S. PATENT DOCUMENTS

| | | | |
|---|---|---|---|
| 3,760,024 | 9/1973 | Cattanach | 585/415 |
| 3,827,968 | 8/1974 | Givens et al. | 585/415 |
| 3,843,741 | 10/1974 | Yan | 585/415 |
| 3,845,150 | 10/1974 | Yan et al. | 585/415 |
| 4,414,423 | 11/1983 | Miller | 585/517 |

*Primary Examiner*—John Doll
*Assistant Examiner*—A. Pal

[57] ABSTRACT

This invention relates to a two-stage conversion of olefins into aromatic hydrocarbon mixtures by contacting them in the first stage with a crystalline metal silicate and in the second stage with a crystalline gallium silicate.

28 Claims, No Drawings

PROCESS FOR THE PREPARATION OF AN AROMATIC HYDROCARBON MIXTURE

FIELD OF THE INVENTION

The invention relates to a process for the preparation of an aromatic hydrocarbon mixture from mono-olefins with two to four carbon atoms per molecule or from aliphatic hydrocarbon mixtures, at least 20 wt.% of which consists of the said olefins.

BACKGROUND OF THE INVENTION

Mono-olefins with two to four carbon atoms per molecule can be converted at a temperature of 325°–700° C. into aromatic hydrocarbon mixtures by contacting the olefins with a catalyst containing a crystalline aluminum silicate with a special structure. Such crystalline aluminum silicates are characterized by the fact that after calcination in air for one hour at 500° C. they possess the following distinguishing features:

(a) an X-ray powder diffraction pattern containing as strongest lines the four lines listed in Table A, and

TABLE A

| d(Å) |
|---|
| 11.1 ± 0.1 |
| 10.0 ± 0.1 |
| 3.84 ± 0.07 |
| 3.72 ± 0.06 |

(b) when the composition of the silicate is expressed in moles of the oxides, the $SiO_2/Al_2O_3$ mol. ratio is 25–400.

The above mentioned process results in a product in which, besides the desired $C_5^+$ hydrocarbons, $C_4^-$ hydrocarbons formed as byproducts also occur. The $C_5^+$ fraction present in the product is more valuable according as it has a higher aromatic content.

The aromatic content of the $C_5^+$ fraction obtained depends to a large extent on the chosen reaction temperature and $SiO_2/Al_2O_3$ mol. ratio of the crystalline silicate. According as a higher reaction temperature and/or a crystalline silicate with a lower $SiO_2/Al_2O_3$ mol. ratio is used in the process, a product is obtained whose $C_5^+$ fraction has a higher aromatic content. For both these measures, however, the preparation of a product whose $C_5^+$ fraction has a higher aromatic content is accompanied by a reduction in the yield of the $C_5^+$ fraction. A particular relationship exists between the increase in the aromatic content of the $C_5^+$ fraction and the reduction in the yield of the $C_5^+$ fraction, so that, in principle, for every aromatic content of the $C_5^+$ fraction being prepared, there is a particular potential yield of the $C_5^+$ fraction. This relationship is unfavorable to the extent that only low yields of $C_5^+$ fractions with a relatively high aromatic content can be obtained. Since a possible application of the process on a commercial scale depends not only on the aromatic content of the $C_5^+$ fraction, but also on the potential yield of that $C_5^+$ fraction, there is a practical limit to the maximum aromatic content of the $C_5^+$ fraction being prepared, due to the fact that the corresponding yield of the $C_5^+$ fraction must still be acceptable.

It has recently been found that considerably better results can be obtained in the above-mentioned process if, as crystalline silicate with the previously mentioned special structure, a silicate containing gallium instead of aluminum is used, and if, moreover, the following two requirements are met:

(a) when the composition of the gallium silicate is expressed in moles of the oxides, the $SiO_2/Ga_2O_3$ mol. ratio should be 25–250, and (b) if the gallium silicate has a $SiO_2/Ga_2O_3$ mol. ratio of 100–250, the catalyst should be subjected one or more times to a two-stage treatment, hereinafter termed "redox treatment" for short, comprising a first stage in which the catalyst is contacted for at least 15 minutes at a temperature of 350°–700° C. with a hydrogen-containing reducing gas, followed by a second stage in which the catalyst is contacted for at least 15 minutes at a temperature of 350°–700° C. with an oxygen-containing oxidizing gas.

In the case of the present crystalline gallium silicates corresponding with the previously mentioned crystalline aluminum silicates, the higher the reaction temperature and/or the lower the $SiO_2/Ga_2O_3$ mol. ratio of the silicate employed, the higher the aromatic content of the $C_5^+$ fraction of the product obtained, and also that for both measures the preparation of a product whose $C_5^+$ fraction has a higher aromatic content is accompanied by a reduction in the yield of the $C_5^+$ fraction. For the crystalline gallium silicates, there is also a relationship between the increase in the aromatic content of the $C_5^+$ fraction and the reduction in the yield of the $C_5^+$ fraction, whereby, in principle, for every aromatic content of the $C_5^+$ fraction being prepared there is a particular potential yield of that $C_5^+$ fraction. The important difference between the crystalline aluminum silicates and the present crystalline gallium silicates is that the previously mentioned relationship for the gallium silicates is considerably more favorable, so that considerably higher yields of $C_5^+$ fractions with a relatively high aromatic content can be obtained than is the case for the aluminum silicates.

It has now been found that further improvement of the relationship between the yield of $C_5^+$ fraction and the aromatic content thereof can be achieved by carrying out the conversion in two stages. First of all, the feed is contacted in a first stage at a temperature of 325°–550° C. with a catalyst containing a crystalline metal silicate with the previously mentioned special structure, which silicate is further characterized in that in the formula representing the composition of the silicate expressed in moles of the oxides and wherein, apart from $SiO_2$, one or more oxides of a trivalent metal selected from aluminum, iron, gallium and boron are present, the $SiO_2/X_2O_3$ mol. ratio amounts to 25–400. Subsequently, the reaction product from the first stage is separated into a $C_4^-$ and a $C_5^+$ fraction, and the $C_4^-$ fraction is contacted in a second stage at a temperature of 450°–700° C. that is at least 50° C. higher than the temperature employed in the first stage with the previously mentioned catalyst, defined in the description of the improved single-stage process, that contains a crystalline gallium silicate. Finally, the reaction product of the second stage is separated into a $C_4^-$ and $C_5^+$ fraction and the separated $C_5^+$ fractions are mixed. Comparison of the results obtained during the preparation of aromatic hydrocarbon mixtures on the basis of a given feed and with use of either the now proposed two-stage process or the previously described improved single-stage process, employing the defined catalyst containing a crystalline gallium silicate has revealed that if the processes were aimed at the preparation of a $C_5^+$ fraction with a particular aromatic content, the two-stage process gave a higher yield of $C_5^+$ fractions, whereas if the processes were aimed at a given yield of $C_5^+$ fraction, the two-stage process produced a $C_5^+$ fraction with a higher aromatic content. In the case of the two-stage process now proposed, it is essential that the $C_4^-$ fraction of the product from the first stage is used as feed for the second stage, as it has been found that if the $C_5^+$ fraction of the product from the first stage or the total reaction product of the first stage is used as feed for the second stage instead of the $C_4^-$ fraction of the product of the first stage, a result is achieved which is even less favorable than that obtained in the improved single-stage process.

SUMMARY OF THE INVENTION

The present patent application therefore relates to a process for the preparation of an aromatic hydrocarbon mixture, wherein one or more mono-olefins with two to four carbon atoms per molecule or aliphatic hydrocarbon mixtures, at least about 20 wt.% of which consists of the said olefins, are contacted in a first stage at a temperature of between about 325° and about 500° C. with a catalyst containing a crystalline gallium silicate, which silicate has the following distinguishing features after calcination for one hour in air at about 500° C.:

(a) an X-ray powder diffraction pattern that contains as strongest lines the four lines listed in Table A, and (b) in the formula which gives the composition of the silicate expressed in moles of the oxides and wherein, apart from $SiO_2$, one or more oxides of a trivalent metal selected from aluminum, iron, gallium and boron are present, the $SiO_2/X_2O_3$ mol. ratio is between about 25 and about 400, wherein the reaction product of the first stage is separated into a $C_4^-$ fraction and a $C_5^+$ fraction, wherein the $C_4^-$ fraction is contacted in a second stage at a temperature of about 450°-700° C. that is at least about 50° C. higher than the temperature employed in the first stage with a catalyst containing a crystalline gallium silicate, which silicate has the following distinguishing features after calcination for one hour in air at about 500° C.

(a) an X-ray powder diffraction pattern that contains as strongest lines the four lines listed in Table A, and (b) in the formula which gives the composition of the silicate expressed in moles of the oxide the $SiO_2/Ga_2O_3$ mol. ratio is between about 25 and about 250, wherein the reaction product of the second stage is separated into a $C_4^-$ fraction and a $C_5^+$ fraction, wherein the separated $C_5^+$ fractions are mixed and wherein, if the gallium silicate present in the catalyst for the second stage has an $SiO_2/Ga_2O_3$ ratio of 100-250, the catalyst is subjected one or more times to the abovementioned redox treatment.

DESCRIPTION OF THE PREFERRED EMBODIMENTS

The starting material for the process according to the invention should be one or more mono-olefins having two to four carbon atoms per molecule or aliphatic hydrocarbon mixtures, at least about 20 wt.% of which consists of the said olefins. The mono-olefins with two to four carbon atoms per molecule, which should form at least about 20 wt.% of the feed, are ethylene, propylene, butylene-1, butylene-2 and iso-butylene. If a hydrocarbon mixture is employed that in addition to the said $C_4^-$ monoolefins also contains other aliphatic hydrocarbons, these other hydrocarbons may be paraffins, di-olefins or $C_5^+$ mono-olefins. In the process according to the invention, a feed is preferably employed which consists of at least about 75 wt.% and in particular substantially completely of one or more mono-olefins with three or four carbon atoms per molecule. A very suitable feed for the present process is a hydrocarbon mixture consisting substantially of $C_3$ and/or $C_4$ mono-olefins, this mixture being obtained as byproduct of the catalytic or thermal cracking of hydrocarbons, in particular the steam cracking of hydrocarbons for the preparation of ethylene.

In the process according to the invention, a catalyst containing a crystalline metal silicate, defined inter alia by the X-ray powder diffraction pattern of the silicate after calcination for one hour in air at about 500° C., is used in both the first and second stages. This should contain as strongest lines the four lines given in Table A. The complete X-ray powder diffraction pattern of a typical example of the present crystalline metal silicates after calcination for one hour in air at 500° C. is represented in Table B.

TABLE B

| d (Å) | Rel. int. | d (Å) | Rel. int. |
|---|---|---|---|
| 11.1 | 100 | 3.84 (D) | 57 |
| 10.0 (D) | 70 | 3.72 (D) | 31 |
| 8.93 | 1 | 3.63 | 16 |
| 7.99 | 1 | 3.47 | <1 |
| 7.42 | 2 | 3.43 | 5 |
| 6.68 | 7 | 3.34 | 2 |
| 6.35 | 11 | 3.30 | 5 |
| 5.97 | 17 | 3.25 | 1 |
| 5.70 | 7 | 3.05 | 8 |
| 5.56 | 10 | 2.98 | 11 |
| 5.35 | 2 | 2.96 | 3 |
| 4.98 (D) | 6 | 2.86 | 2 |
| 4.60 | 4 | 2.73 | 2 |
| 4.35 | 5 | 2.60 | 2 |
| 4.25 | 7 | 2.48 | 3 |
| 4.07 | 2 | 2.40 | 2 |
| 4.00 | 4 | | |

(D) = doublet

In the process according to the invention, a catalyst should be employed in the first stage that contains a crystalline metal silicate wherein one or more trivalent metals X are present and wherein the $SiO_2/X_2O_3$ mol. ratio is about 25-400. Crystalline metal silicates having a $SiO_2/X_2O_3$ mol. ratio of about 25-250 are preferred. The first stage of the process is preferably carried out at a temperature of about 350°-475° C., a pressure of about 1-20 bar and in particular of about 1-10 bar and a space velocity of about 0.1-10 kg.-$kg^{-1}$.$hour^{-1}$ and in particular of about 0.5-5 kg.$kg^{-1}$.$hour^{-1}$.

The second stage of the process according to the invention is preferably carried out at a temperature of about 500°-600° C. and in particular at a temperature which is at least about 75° C. higher than the temperature used in the first stage, a pressure of about 1-20 bar and in particular of about 1-10 bar and a space velocity of about 0.1-10 and in particular of about 0.2-5 kg first-stage feed per kg second-stage catalyst per hour.

In the process according to the invention, a catalyst containing a crystalline gallium silicate with an $SiO_2/Ga_2O_3$ mol. ratio of about 25-250 should be used. If the crystalline gallium silicate employed in the second stage has an $SiO_2/Ga_2O_3$ mol. ratio of about 100-250, it should be subjected one or more times to the above-described redox treatment. Although crystalline gallium silicates with an $SiO_2/Ga_2O_3$ mol. ratio of less than about 100 are suitable as such for use in the second stage of the process according to the invention, they are also preferably subjected one or more times to the above-described redox treatment. In the process according to the invention, preferred crystalline gallium silicates for employment in the second stage have an $SiO_2/Ga_2O_3$ mol. ratio of about 60-220. When employing a crystalline gallium silicate with a maximum $SiO_2/Ga_2O_3$ mol. ratio of about 110 in the second stage, the redox treatment is preferably not performed more than three times. When employing a crystalline gallium silicate with a $SiO_2Ga_2O_3$ mol. ratio of more than about 110, but not more than about 130 in the second stage, the redox treatment is preferably performed at least three times, but not more than ten times. When employing a crystalline gallium silicate with an $SiO_2/Ga_2O_3$ mol. ratio of more than about 130, but not more than about 220 in the second stage, the silicate is preferably first subjected to calcination at a temperature of about 600°-1000° C., after which the redox treatment is performed on it at least three times, but not more than ten times.

During the first stage of the redox treatment, the catalyst should be contacted for at least 15 minutes at a temperature of about 350°-700° C. with a hydrogen-containing reducing gas. The first stage of the redox treatment can, in principle, be performed in two ways. In the first place, the hydrogen-containing reducing gas can be fed to the catalyst from outside. In that case, a gas is preferably employed that contains at least about 20 vol.% and in particular at least about 40 vol.% hydrogen. The gas employed can very suitably contain, besides hydrogen, either mainly nitrogen or mainly carbon monoxide or mainly $C_4-$ hydrocarbons. Suitable gases which, besides hydrogen, contain mainly carbon monoxide, can be obtained as synthesis gas from a highly carbonaceous material, such as coal, by gasification, or from light hydrocarbons, such as natural gas, by steam reforming or partial oxidation. Suitable gases which, besides hydrogen, contain mainly $C_4-$ hydrocarbons can be obtained as byproduct from the catalytic conversion of hydrocarbons in the presence of hydrogen, such as cracking, isomerization and reforming. In the second place, the hydrogen-containing reducing gas can be produced in situ by contacting the catalyst for a maximum of five hours with a hydrocarbon or a hydrocarbon mixture. A very suitable hydrocarbon or hydrocarbon mixture would in this case be the feed employed in the present process.

In the second stage of the redox treatment, the catalyst should be contacted for at least 15 minutes at a temperature of about 350°-700° C. with an oxygen-containing oxidizing gas. The gas employed preferably contains at least about 5 vol.% and in particular at least about 10 vol.% oxygen. The second stage of the redox treatment can very suitably be performed using a gas which, besides oxygen, contains either mainly nitrogen or otherwise mainly nitrogen, carbon monoxide and carbon dioxide. A suitable gas that, besides oxygen, contains mainly nitrogen is air. Suitable gases which, besides oxygen, contain mainly nitrogen, carbon monoxide and carbon dioxide are offgases obtained during the removal of carbon by means of an excess of air from deactivated hydrocarbon conversion catalysts. Preferably, the two stages of the redox treatment are performed at a temperature of about 400°-650° C. and in particular at a temperature of about 475°-575° C. It is also preferable that the two stages of the redox treatment be performed at the same temperature.

The crystalline metal silicates employed in the process according to the invention can very suitably be prepared from an aqueous mixture containing the following compounds: one or more compounds of an alkali metal (M), one or more organo(R)-nitrogen (N) compounds containing an organic cation or from which an organic cation is formed during the preparation of the silicate, one or more silicon compounds and one or more compounds of a trivalent metal X. For the preparation of the crystalline gallium silicates that are used in the second stage of the process, only aqueous mixtures, wherein only one or more gallium compounds are present as compounds of a trivalent metal X, are of course suitable. Preparation is effected by maintaining the mixture at an elevated temperature until the silicate has been formed and then separating the silicate crystals from the mother liquor and washing, drying and calcining the crystals. The aqueous mixture from which the silicates are prepared should contain the various compounds in the following molar ratios, except for the organic nitrogen compounds, expressed in moles of the oxides:

$M_2O:SiO_2 = 0.01-0.35$,
$RN:SiO_2 = 0.02-1.0$,
$SiO_2:X_2O_3 = 25-1000$, and
$H_2O:SiO_2 = 5-65$.

The silicates can very suitably be prepared from a basic mixture containing a quaternary ammonium compound as organic nitrogen compound, a sodium compound as alkali metal compound and amorphous silica as silicon compound.

The silicates prepared according to the above method contain alkali metal ions. By means of suitable exchange techniques, these can be replaced by other cations, such as hydrogen ions or ammonium ions. The crystalline metal silicates employed in the process according to the invention preferably have an alkali metal content of less than about 0.05 wt.%. In the process according to the invention the crystalline metal silicates can be used as such or in combination with a binding material, such as kaolin or bentonite.

The invention will now be illustrated with the aid of the following example which is intended for illustration and not to be construed as limiting the invention.

EXAMPLE

A crystalline aluminum silicate (silicate 1) and a crystalline gallium silicate (silicate 2) were prepared by heating mixtures of NaOH, amorphous silica, $(C_3H_7)_4NOH$ and either $Al(NO_3)_3$, or $Ga(NO_3)_3$ in water in an autoclave under autogenous pressure for 24 hours at 150° C. After the reaction mixtures had cooled down, the resulting silicates were filtered off, washed with water until the pH of the wash water was about 8 and dried at 120° C. After calcination for one hour in air at 500° C., the silicates 1 and 2 had the following properties:

(a) an X-ray powder diffraction pattern corresponding substantially with that given in Table B, and (b) an $SiO_2Al_2O_3$ mol. ration of 250 for silicate 1 and an $SiO_2/Ga_2O_3$ mol. ratio of 70 for silicate 2.

From silicates 1 and 2, silicates I and II were prepared respectively by boiling silicates 1 and 2 with 1.0 molar $NH_4NO_3$ solution, washing with water, again boiling with 1.0 molar $NH_4NO_3$ solution and washing, drying at 120° C. and calcining at 500° C. Silicate II was subjected three times to a redox treatment comprising a first stage in which the silicate was contacted for 30 minutes with n-butane at a temperature of 550° C., a pressure of 1.5 bar and a space velocity of 8 kg.kg.$^{-1}$.hour$^{-1}$, followed by a second stage in which the silicate was contacted for 1 hour with air at a temperature of 550° C. and a pressure of 1.5 bar. In this way silicate IIA was obtained from silicate II.

Silicates I and IIA were tested in a series of eight experiments (experiments 1-8) for the preparation of $C_5^+$ aromatic hydrocarbon mixtures from iso-butylene. All experiments were performed at a pressure of 1.5 bar. Experiments 1-3 were performed in one stage at a space velocity of 2 kg.kg.$^{-1}$.hour$^{-1}$ in a reactor containing a solid catalyst bed. Experiments 4-8 were performed in two stages at a space velocity of 2 kg.kg.$^{-1}$.hour$^{-1}$ in the first stage and at a temperature of 575° C. using silicate IIA as catalyst in the second stage, in two reactors each containing a solid catalyst bed. In experiments 4-6, the product of the first stage was separated into a $C_4^-$ fraction and a $C_5^+$ fraction, the $C_4^-$ fraction was used as feed for the second stage, the product of the second stage was likewise separated into a $C_4^-$ fraction and a $C_5^+$ fraction and the two $C_5^+$ fractions were combined. In experiment 7, the product of the first stage was separated into a $C_4^-$ fraction and a $C_5^+$ fraction, the $C_5^+$ fraction was used as feed for the second stage and the product of the second stage was separated into a $C_4^-$ fraction and a $C_5^+$ fraction. In experiment 8, the total product of the first stage was used as feed for the second stage and the product of the second stage was separated into a $C_4^-$ fraction and a $C_5^+$ fraction. In all experiments, virtually complete conversion of the feed was accomplished. The temperature at which experiments 1-3 and the first stage of experiments 4-8 were performed and the space velocities at which the second stage of experiments 4-8 were performed are stated in Table C. That Table also includes the results of the experiments.

Of experiments 1-8, only experiments 4 and 5 are experiments according to the invention. The other experiments fall outside the scope of the invention. They are included in the patent application for the purpose of comparison. The comparative experiments 1-3 were performed in one stage. In the comparative experiments 6-8, despite the fact that the process was carried out in two stages the results were nonetheless unsatisfactory, the reasons being that in experiment 6 the temperature difference between the two stages amounted to merely 25° C., in experiment 7 the $C_5^+$ fraction of the product in the first stage was used as feed for the second stage and in experiment 8 the total product of the first stage was used as feed for the second stage.

Comparison of experiments 1 (with aluminum silicate) and 2 and 3 (with gallium silicate) reveals the improvement that can be achieved by substituting gallium silicate for aluminum silicate in the single-stage process. At an identical aromatic content of the $C_5^+$ fraction (48 wt.%), the gallium silicate gives a far higher $C_5^+$ fraction yield (72 wt.%) than the aluminum silicate does (63%), while at an identical $C_5^+$ fraction yield (63 wt.%) the gallium silicate yields a $C_5^+$ fraction with a much higher aromatic content (83 wt.%) than the aluminum silicate (48%).

Comparison of experiments 4 and 5 (two-stage in accordance with the invention) with 2 (single-stage with gallium silicate) reveals the further improvement arising from the process according to the invention. At a virtually identical aromatic content of the $C_5^+$ fraction (48-50 wt.%), the two-stage process gives a far higher $C_5^+$ fraction yield (84 wt.%) than the single-stage process (72 wt.%), while at a virtually identical $C_5^+$ fraction yield (72-74% wt.%), the two-stage process yields a $C_5^+$ fraction with a far higher aromatic content (68 wt.%) than the single-stage process (48 wt.%).

Comparison of experiments 6-8 (two stage not according to the invention) and 3 (single-stage with gallium silicate) reveals that at a virtually identical aromatic content of the $C_5^+$ fraction (82-85 wt.%), the two-stage experiment 6 gives a virtually identical yield (62 wt.%) and the two-stage experiments 7 and 8 even give a far lower $C_5^+$ yield (42-49 wt.%) than the single-stage experiment (63 wt.%).

TABLE C

| Experiment No. | 1 | 2 | 3 | 4 | 5 | 6 | 7 | 8 |
|---|---|---|---|---|---|---|---|---|
| Silicate as catalyst in the first stage | I | IIA | IIA | I | I | I | I | I |
| Temperature in the first stage, °C. | 450 | 350 | 550 | 430 | 475 | 550 | 430 | 430 |
| Space velocity in second stage in terms of feed for first stage, kg.kg.$^{-1}$.hour$^{-1}$ | — | — | — | 2 | 1 | 1 | 2 | 2 |
| $C_5^+$ fraction yield, wt. % | 63 | 72 | 63 | 84 | 74 | 62 | 42 | 49 |
| Aromatic content of the $C_5^+$ fraction, wt. % | 48 | 48 | 83 | 50 | 68 | 82 | 85 | 84 |

I claim:

1. A process for the preparation of an aromatic hydrocarbon mixture, which comprises contacting a feed comprising one or more olefins with two to four carbon atoms per molecule or aliphatic hydrocarbon mixtures, at least 20 wt.% of which consists of the said olefins, at a temperature of between 325° and 550° C. with a catalyst containing a crystalline metal silicate, which silicate has the following distinguishing features after calcination for one hour in air at 500° C.:

(a) an X-ray powder diffraction pattern containing as strongest lines the four lines listed in Table A as follows, and

TABLE A

| d(Å) |
|---|
| 11.1 ± 0.1 |
| 10.0 ± 0.1 |
| 3.84 ± 0.07 |
| 3.72 ± 0.06 |

(b) when the composition of the silicate is expressed in moles of the oxides, and wherein, apart from $SiO_2$, one or more oxides of a trivalent metal (X) selected from aluminum, iron, gallium and boron are present, the $SiO_2/X_2O_3$ mol. ratio is between 25 and 400, that the reaction product from the first stage is separated into a $C_4^-$ and a $C_5^+$ fraction, that the $C_4^-$ fraction is contacted in a second stage at a temperature of 450°-700° C. that is at least 50° C. higher than the temperature employed in the first stage with a catalyst that contains a crystalline gallium silicate, which silicate has the following distinguishing features after calcination for one hour in air at 500° C.:
  (a) an X-ray powder diffraction pattern than contains as strongest lines the four lines listed in Table A, and
  (b) when the composition of the silicate is expressed in moles of the oxides, the $SiO_2/Ga_2O_3$ mol. ratio is between 25 and 250, that the reaction product of the second stage is separated into a $C_4^-$ fraction and a $C_5^+$ fraction, that the separated $C_5^+$ fractions are mixed and that, if the gallium silicate present in the second-stage catalyst has an $SiO_2/Ga_2O_3$ ratio of 100-250, the catalyst is subjected one or a number of times to a two-stage treatment ("redox treatment") comprising a first stage in which the catalyst is contacted for at least 15 minutes at a temperature of 350°-700° C. with a hydrogen-containing reducing gas, followed by a second stage in which the catalyst is contacted for at least 15 minutes at a temperature of 350°-700° C. with an oxygen-containing oxidizing gas.

2. The process of claim 1, wherein it is applied to a feed, 75 wt.% of which consists of one or more mono-olefins with three or four carbon atoms per molecule.

3. The process of claim 2, wherein the feed consists substantially of one or more mono-olefins with three or four carbon atoms per molecule.

4. The process of claim 1, wherein the first stage is carried out at a pressure of 1-20 bar and a space velocity of 0.1-10 $kg.kg^{-1}.hour^{-1}$.

5. The process of claim 1, wherein the first stage is carried out at a temperature of 350°-475° C., a pressure of 1-10 bar and a space velocity of 0.5-5 $kg.kg^{-1}.hour^{-1}$.

6. The process of claim 1, wherein in the first stage a crystalline metal silicate is used with a $SiO_2/X_2O_3$ mol. ratio of 25-250.

7. The process of claim 1, wherein the second stage is carried out at a pressure of 1-20 bar and a space velocity of 0.1-10 kg first-stage feed per kg second-stage catalyst per hour.

8. The process of claim 1, wherein the second stage is carried out at a temperature of 500°-600° C., a pressure of 1-10 bar and a space velocity of 0.2-5 kg first-stage feed per kg second-stage catalyst per hour.

9. The process of claim 1, wherein the second stage is carried out at a temperature which is at least 75° C. higher than the temperature employed in the first stage.

10. The process of claim 1, wherein in the second stage a crystalline gallium silicate is used with a $SiO_2/Ga_2O_3$ mol. ratio of 60-220.

11. The process of claim 1, wherein in the second stage a crystalline gallium silicate is used with a $SiO_2/Ga_2O_3$ mol. ratio of less than 100, that is subjected one or more times to the redox treatment.

12. The process of claim 1, wherein in the second stage a crystalline gallium silicate is used with a maximum $SiO_2/Ga_2O_3$ mol. ratio of 110, that is subjected to the redox treatment not more than three times.

13. The process of claim 1, wherein in the second stage a crystalline gallium silicate is used with an $SiO_2/Ga_2O_3$ mol. ratio of more than 110, but not more than 130, that is subjected to the redox treatment at least three times, but not more than ten times.

14. The process of claim 1, wherein in the second stage crystalline gallium silicate is used with an $SiO_2/Ga_2O_3$ mol. ratio of more than 130, but not more than 220, which is subjected first to calcination at a temperature of 600°-1000° C. and then at least three times but not more than ten times to the redox treatment.

15. The process of claim 1, wherein the first stage of the redox treatment is carried out using a hydrogen-containing reducing gas supplied to the catalyst from outside.

16. The process of claim 1, wherein the reducing gas contains at least 20 vol.% hydrogen.

17. The process of claim 1, wherein the reducing gas contains at least 40 vol.% hydrogen.

18. The process of claim 1, wherein the reducing gas is chosen from the group formed by gases which, besides hydrogen, consist either mainly of nitrogen or mainly of carbon monoxide or mainly of $C_4^-$ hydrocarbons.

19. The process of claim 1, wherein the first stage of the redox treatment is carried out by using a hydrogen-containing reducing gas produced in situ by contacting the catalyst for up to five hours with a hydrocarbon or hydrocarbon mixture.

20. The process of claim 1, wherein the oxidizing gas contains at least 5 vol.% oxygen.

21. The process of claim 1, wherein the oxidizing gas contains at least 10 vol.% oxygen.

22. The process of claim 1, wherein the oxidizing gas is chosen from the group formed by gases which, besides oxygen, consist either mainly of nitrogen or mainly of nitrogen, carbon monoxide and carbon dioxide.

23. The process of claim 1, wherein both stages of the redox treatment are carried out at a temperature of 400°-650° C.

24. The process of claim 1, wherein both stages of the redox treatment are carried out at a temperature of 475°-575° C.

25. The process of claim 1, wherein both stages of the redox treatment are carried out at the same temperature.

26. The process of claim 1, wherein the crystalline metal silicates are prepared from an aqueous mixture containing the following compounds: one or more compounds of an alkali metal (M), one or more organo(R)-nitrogen (N) compounds containing an organic cation or from which an organic cation is formed during the preparation of the silicate, one more silicon compounds and one or more compounds of a trivalent metal X, and in which mixture the various compounds are present in the following molar ratios, except for the organic nitrogen compounds, expressed in moles of the oxides:

$M_2O:SiO_2=0.01-0.35$,
$RN:SiO_2=0.02-1.0$,
$SiO_2:X_2O_3=25-1000$, and
$H_2O:SiO_2=5-65$ by maintaining the aqueous mixture at an elevated temperature until the silicate has been formed and then separating the silicate crystals from the mother liquor and calcining them.

27. The process according to claim 26, wherein the aqueous mixture contains a quaternary ammonium compound as organo-nitrogen compound, a sodium compound as alkali metal compound and amorphous silica as silicon compound.

28. The process of claim 1, wherein the crystalline metal silicates have an alkali metal content of less than 0.05 wt.%.

* * * * *